(12) United States Patent
Stats

(10) Patent No.: US 8,262,630 B2
(45) Date of Patent: *Sep. 11, 2012

(54) VASCULAR ACCESS PORT WITH INTEGRAL ATTACHMENT MECHANISM

(75) Inventor: Jason R. Stats, Layton, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/052,730

(22) Filed: Mar. 21, 2011

(65) Prior Publication Data

US 2011/0230842 A1    Sep. 22, 2011

Related U.S. Application Data

(62) Division of application No. 11/348,182, filed on Feb. 6, 2006, now Pat. No. 7,909,804.

(60) Provisional application No. 60/650,693, filed on Feb. 7, 2005.

(51) Int. Cl.
*A61M 37/00* (2006.01)

(52) U.S. Cl. ........ 604/288.01; 604/75; 606/144; 606/145; 606/146; 606/219; 606/139; 607/132

(58) Field of Classification Search ........ 604/175, 604/288.01; 606/139, 144–146, 219; 607/132
See application file for complete search history.

(56) References Cited

U.S. PATENT DOCUMENTS

| 3,946,740 | A | * | 3/1976 | Bassett ............... 606/145 |
| 4,027,608 | A | | 6/1977 | Arbuckle |
| 4,471,781 | A | | 9/1984 | Di Giovanni et al. |
| 4,621,640 | A | * | 11/1986 | Mulhollan et al. ............ 606/144 |
| 4,673,394 | A | | 6/1987 | Fenton, Jr. et al. |
| 5,306,281 | A | | 4/1994 | Beurrier |
| 5,540,648 | A | | 7/1996 | Yoon |
| 5,713,858 | A | | 2/1998 | Heruth et al. |
| 5,860,992 | A | | 1/1999 | Daniel et al. |
| 6,048,351 | A | * | 4/2000 | Gordon et al. ............ 606/144 |
| 6,663,641 | B1 | * | 12/2003 | Kovac et al. ............ 606/144 |
| 6,955,643 | B2 | | 10/2005 | Gellman et al. |

(Continued)

FOREIGN PATENT DOCUMENTS
EP    1346753 A2    9/2003
(Continued)

OTHER PUBLICATIONS

PCT/US2004/030053 filed Sep. 15, 2004 entitled Implantable Device Fastening System and Method of Use.
(Continued)

*Primary Examiner* — Matthew F Desanto
*Assistant Examiner* — Scott Medway
(74) *Attorney, Agent, or Firm* — Rutan & Tucker, LLP

(57) ABSTRACT

An implantable port with an integral attachment mechanism. The implantable port includes one or more suture needles enclosed within a port body, the suture needle(s) coupled to a movable member such that movement of the movable member results in movement of the suture needle(s) out of the port body and into the tissue of a body into which it is implanted. The movable member can be a cam or tensioning member that rotates about a central port axis. The movable member can be coupled to a gear to permit movement of the movable member following implantation of the port within a subcutaneous pocket.

11 Claims, 5 Drawing Sheets

U.S. PATENT DOCUMENTS

| | | |
|---|---|---|
| 6,997,932 B2 * | 2/2006 | Dreyfuss et al. .............. 606/139 |
| 7,004,951 B2 * | 2/2006 | Gibbens, III .................. 606/144 |
| 7,374,557 B2 | 5/2008 | Conlon et al. |
| 7,540,857 B2 | 6/2009 | Backman et al. |
| 7,909,804 B2 | 3/2011 | Stats |
| 2003/0216613 A1 | 11/2003 | Suzuki et al. |
| 2004/0254536 A1 | 12/2004 | Conlon et al. |
| 2004/0254537 A1 | 12/2004 | Conlon et al. |
| 2005/0131352 A1 | 6/2005 | Conlon et al. |
| 2005/0148956 A1 | 7/2005 | Conlon et al. |
| 2005/0277899 A1 | 12/2005 | Conlon et al. |
| 2006/0116648 A1 | 6/2006 | Hamatake |
| 2006/0173424 A1 | 8/2006 | Conlon |
| 2006/0178647 A1 | 8/2006 | Stats |
| 2006/0190039 A1 | 8/2006 | Birk et al. |
| 2006/0235445 A1 | 10/2006 | Birk et al. |
| 2007/0161958 A1 | 7/2007 | Glenn |
| 2007/0293829 A1 | 12/2007 | Conlon et al. |
| 2009/0093768 A1 | 4/2009 | Conlon et al. |
| 2009/0281503 A1 | 11/2009 | Lampropoulos et al. |

FOREIGN PATENT DOCUMENTS

| | | |
|---|---|---|
| WO | 2005037055 A2 | 4/2005 |
| WO | 2005072627 A1 | 8/2005 |

OTHER PUBLICATIONS

U.S. Appl. No. 11/348,182, filed Feb. 6, 2006 Notice of Allowance dated Oct. 7, 2010.

U.S. Appl. No. 11/348,182, filed Feb. 6, 2006 Non-Final Office Action dated Apr. 14, 2010.

U.S. Appl. No. 11/348,182, filed Feb. 6, 2006 Final Office Action dated Jul. 21, 2009.

U.S. Appl. No. 11/348,182, filed Feb. 6, 2006 Non-Final Office Action dated Dec. 12, 2008.

* cited by examiner

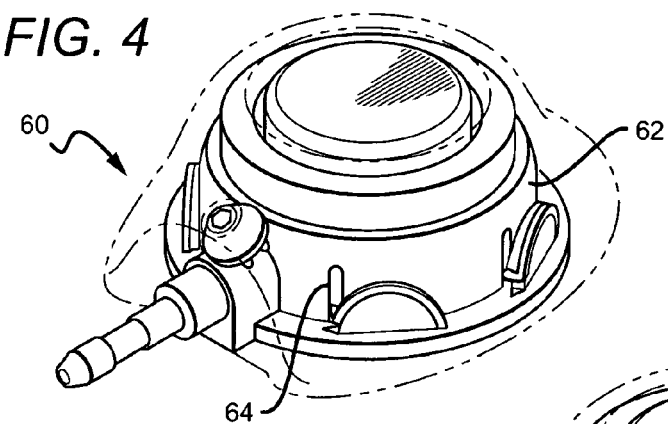
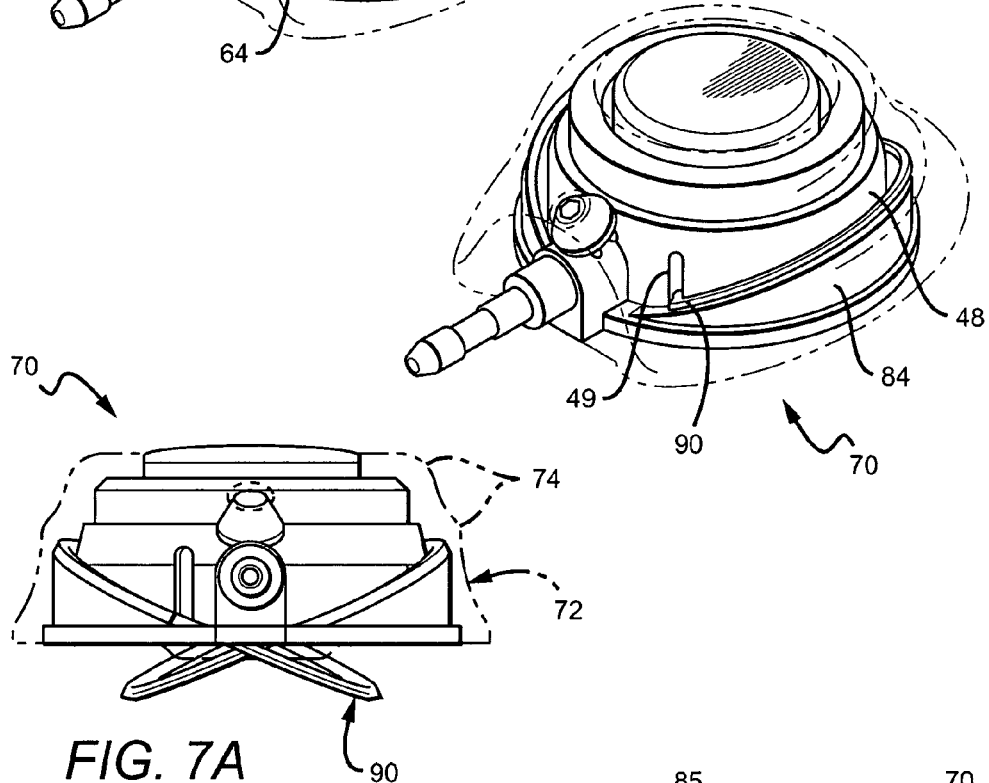
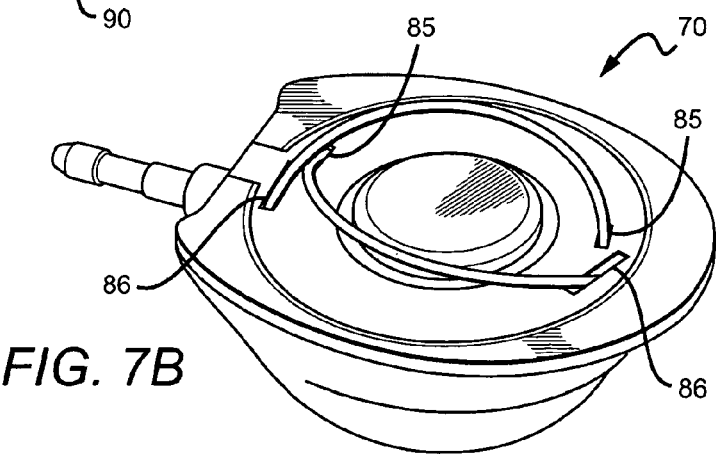

VASCULAR ACCESS PORT WITH INTEGRAL ATTACHMENT MECHANISM

CROSS-REFERENCE TO RELATED APPLICATIONS

This application is a division of U.S. application Ser. No. 11/348,182, filed Feb. 6, 2006, now U.S. Pat. No. 7,909,804, which claims the benefit under 35 U.S.C. §119(e) to U.S. Provisional Application No. 60/650,693, filed Feb. 7, 2005, each of which is incorporated by reference into this application as if fully set forth herein.

BACKGROUND OF THE INVENTION

A variety of subcutaneously implantable access ports have been utilized by clinicians to deliver fluids to, and/or to withdraw fluids from, the blood stream or other subcutaneous cavities inside a patient. One example of such an access port includes a substantially needle-impenetrable housing, which encloses one or more fluid cavities and defines for each of such fluid cavity an access aperture communicating through the housing on the side thereof, which is adjacent to the skin of the patient when the access port is implanted in the body of a patient. A needle-penetrable septum is received in and seals the access aperture. An exit passageway located in a port stem communicates with the fluid cavity or cavities for dispensing medication therefrom to a predetermined location in the body of the patient through an implanted catheter attached to the access port. Typically, the catheter is connected to the access port by placement of the proximal end of the catheter over a port stem. A locking sleeve or ring may be placed over the catheter at the proximal region of the catheter to secure the catheter to the port stem.

Once the access port and catheter have been implanted beneath the skin of a patient, quantities of fluid, such as medication or blood, may be dispensed from the fluid cavity by means of a non-coring needle passed through the skin of the patient and penetrating the septum into the fluid cavity. This fluid may be directed to the distal end of the catheter to an entry point into the venous system of the body of the patient. Blood may also be withdrawn for sampling from the body of the patient through such an access port by piercing the skin of the patient and penetrating the septum with a non-coring needle and applying negative pressure thereto, which causes blood to be drawn through the catheter into the fluid cavity covered by the pierced septum and then out of the body of the patient through the needle. To prevent clotting thereafter, the withdrawal route may be flushed with a saline solution or heparin using again a non-coring needle piercing the skin of the patient and the septum in the same manner as if a medication were being infused.

Both intermittent and continual injections of medication may be dispensed by the access port. Continual access may involve the use of a non-coring needle attached to an ambulatory-type pump or gravity feed bag suspended above the patient. The ambulatory-type pump or the gravity feed bag continually delivers the medication or fluid through the needle to the fluid cavity in the access port and from there through the catheter to the entry point into the venous system.

The access port is generally implanted into a patient's body by creating a subcutaneous pocket and inserting the port, which is connected to a catheter. The access port is implanted just below the patient's skin so that it may be felt by a clinician prior to access with a needle. Typically, the access port is sutured into the subcutaneous pocket to prevent migration thereof as well as to ensure that the port does not turn over such that the septum is not accessible, either of which occurrence would require further surgery. Suturing of the access port requires that the subcutaneous pocket be sized large enough to allow the surgeon to operate and is somewhat time consuming. Usually, the suturing of the access port occurs only on the most-accessible side thereof after insertion into the subcutaneous pocket, meaning that at least one side of the access port is left unsecured. Moreover, the act of suturing carries with it the inherent risks of needle sticks to the operating surgeon. With respect to the patient, the use of sutures (as opposed to a device that does not require the use of sutures) means that removal of the access port is more time consuming for the surgeon and more traumatic for the patient. Further, as the size of the subcutaneous pocket is increased because of the need to utilize sutures, healing time, blood loss, scarring and infection likelihood are increased.

Applicant recognizes the desirability of providing an access port, which does not require sutures for implantation within the body of a patient, which provides a smooth exterior surface prior to implantation for facilitation thereof, and which has an integral attachment mechanism that can be activated following insertion into the subcutaneous pocket such that it can safely be implanted and removed without exposing the clinician to sharp surfaces.

BRIEF SUMMARY OF THE INVENTION

Accordingly, an implantable port with an integral attachment mechanism is described herein. In one embodiment, an implantable port includes an attachment mechanism positioned within a port body, the attachment mechanism including at least one suture needle, the suture needle in contact with a movable member such that movement of the movable member causes at least a portion of the suture needle to exit the port body. In another embodiment, an implantable port includes a port body, including a port top and a port base, the port base including at least one raised section, a suture needle having generally the same shape as the raised section and positioned thereover, and a cam configured for rotation about a central axis of the port, the cam connected to the suture needle such that movement of the cam causes movement of the suture needle.

In one embodiment, a method for attaching a port to a body, the port including a suture needle coupled to a movable member, the suture needle and movable member enclosed within a port body, includes implanting the port into a subcutaneous pocket formed in the body, and moving the movable member from a first position within the port to a second position within the port such that at least a portion of the suture needle exits the port body through an opening.

These and other objectives, embodiments, features and advantages of the present invention will become more apparent to those skilled in the art when taken with reference to the following more detailed description of the invention.

BRIEF DESCRIPTION OF THE DRAWINGS

FIG. 4 is a top perspective view of another embodiment of an implantable port.

FIG. 5 is a top perspective view of yet another embodiment of an implantable port.

FIG. 7A is a front view of the implantable port of FIG. 5, following completion of a suturing process.

FIG. 7B is a bottom perspective view of the implantable port of FIG. 5, following completion of a suturing process.

DETAILED DESCRIPTION OF THE INVENTION

Figure 1:
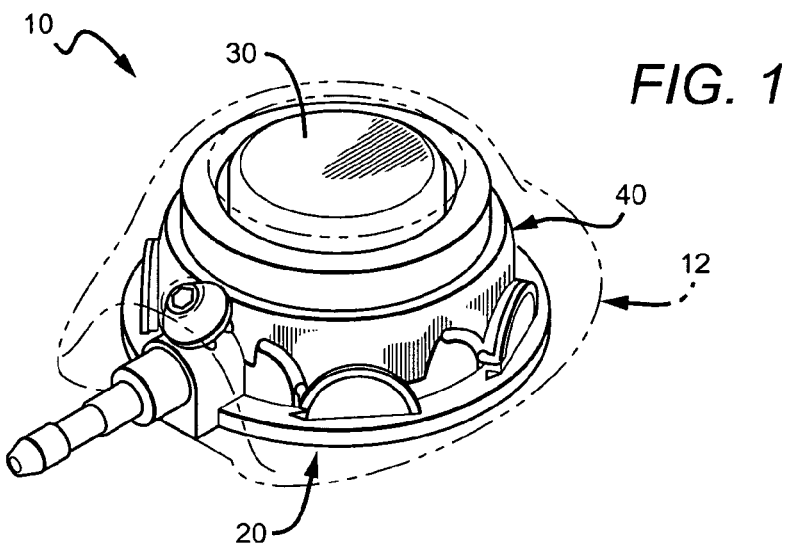
FIG. 1 is a top perspective view of one embodiment of an implantable port.

The following detailed description should be read with reference to the drawings, in which identical reference numbers refer to like elements throughout the different figures. The drawings, which are not necessarily to scale, depict selective embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

The embodiments described herein are directed to a vascular access port with an integral attachment mechanism. Although the examples include implantable ports with a single chamber for holding/dispensing a fluid, it should be understood that the present invention is equally applicable to ports with two or more chambers. Moreover, although certain new port designs are described and illustrated with the inventive attachment mechanism integrated therein, it should be understood that existing port designs could be modified to include integral attachment mechanisms, examples of which are shown and described herein.

Embodiments of the implantable port described herein include an attachment mechanism for attaching the port to a body, the attachment mechanism being enclosed within the port such that a smooth outer profile, safe for handling without risk of accidental needle sticks, is presented to a clinician for use. The attachment mechanisms described herein can include one or more suture needles, which are contained entirely within the port such that no portion of the needle or needles is exposed for potential contact prior to activation of the port in a suturing process. The attachment mechanisms described herein are believed to provide a more effective means than the use of sutures for attachment of a vascular access port within a patient's body. For instance, by providing implantable ports with integral attachment mechanisms, such as those described herein, a smaller than standard subcutaneous pocket, for a given port size, is believed to be necessary, thereby benefiting a patient into which the port is implanted. In addition, by providing implantable ports with integral attachment mechanisms, such as those described herein, a clinician is believed to be able to attach the port to a patient's body in an easier, safer and less time-consuming manner than otherwise possible with conventional processes. Also, implantable ports with attachment mechanisms, such as those described herein, are believed to be more securely attached to a body following the suturing process than ports attached using conventional processes. Further, implantable ports with attachment mechanisms, such as those described herein, are believed to be more easily removed from a body, resulting in a decrease in trauma resulting from typical removal procedures.

Figure 2:
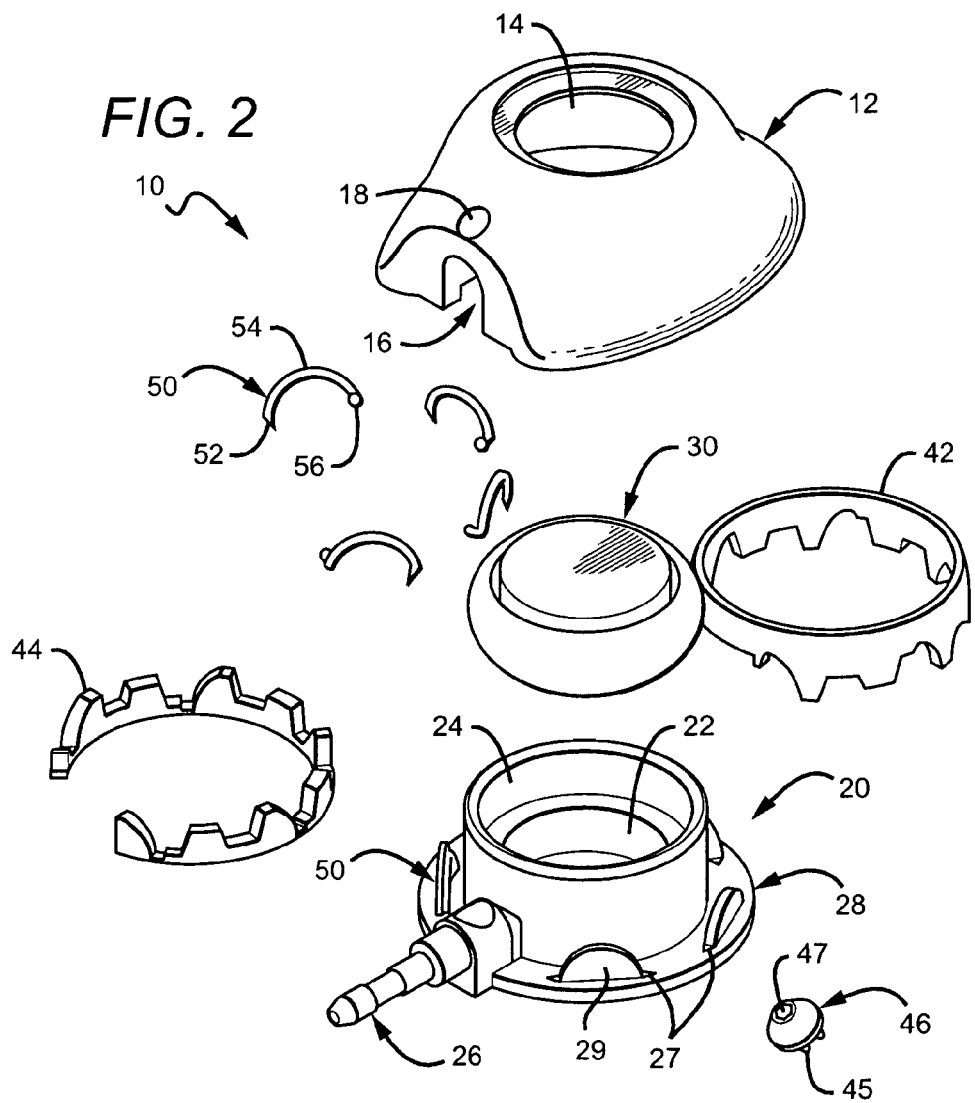
FIG. 2 is an exploded view of the implantable port of FIG. 1.

Referring now to FIGS. 1-2, an implantable port 10 is shown. As best seen in FIG. 2, port 10 includes a top 12, base 20, septum 30, cam 40, gear 46 and suture needles 50. FIG. 1 illustrates the assembled port 10 with the top 12 in phantom so that the component parts can be seen. The top 12, having a smooth profile which is believed to be resistant to tissue ingrowth, includes a first opening 14 for passage of at least a portion of the septum 30, a front slot 16 to accommodate a portion of the base 20, and a second opening 18 to permit access to the gear 46. In one embodiment, the port top 12 is molded by a single-direction mold. The base 20 includes fluid reservoir 22 that is positioned below an upper portion 24 configured to receive a portion of the septum 30 and having a ledge on which the septum 30 rests, preventing the septum 30 from entering the fluid reservoir 22. The base 20 also includes a stem 26 with a lumen in fluid communication with the fluid reservoir 22. The fluid reservoir 22 sits on a platform 28 that includes upright ridges 29 around the circumference thereof. A needle passage 27 through the platform 28 is positioned on each side of each ridge 29 such that at least a portion of the suture needle 50 can pass therethrough. The ridges 29 are configured in the shape of the suture needles 50 such that the suture needles 50 rest atop the ridges 29, one of which suture needle 50 is shown on ridge 29 in FIG. 2. In this embodiment, there are five ridges and five corresponding suture needles; however, any number of suture needles could be incorporated into the port (i.e., one or more) depending on various factors such as port size, suture needle size, intended location, etc., and therefore the invention is not limited to the number of ridges and/or suture needles. Also, while the ridges 29 and suture needles 50 are shown in semi-circle shapes, other shapes are possible and within the scope of the invention.

The suture needles 50, which in one embodiment are made of a radiopaque or other material suitable for imaging, include a pointed tip 52, a body 54, and a post 56 arranged at an angle with respect to the tip 52 and body 54 of the needle 50. In this embodiment, the angle is approximately 90 degrees such that the post 56 is arranged generally perpendicular to the body 54 and tip 52, although other angles are possible and within the scope of the invention. The post 56 includes an enlarged end for interaction with the cam 40 as will be described more completely below. In other embodiments, the post includes other types of interaction mechanisms, such as a roughened surface, a formed section to fit into a corresponding section of the cam 40, etc. The cam 40 includes two separate components, a top section 42 and a bottom section 44, each with intermeshing wedges. The bottom section 44 is seated between the ridges 29 and an outer surface of the fluid reservoir 22, while the top section 42 is positioned thereover. When the port 10 is fully assembled, at least a portion of the post 56 of each suture needle 50 is positioned in a slot formed between the top section 42 and bottom section 44 such that the suture needles 50 are coupled to the cam 40. As the cam 40 about a central axis of the port, the post 56 is free to move within the slot as it simultaneously tracks over a surface of the ridge 29. It is emphasized that when the wedges of the top section 42 and the wedges of the bottom section 44 are intermeshed, a slot is created therebetween to permit movement of the post 56 therein, such that corresponding movement of the needle 50 is facilitated without binding. Thus, while a certain configuration for the top section 42 and bottom section 44 are shown in FIGS. 1-2, it should be appreciated that other configurations are within the scope of the invention.

Figure 3A:
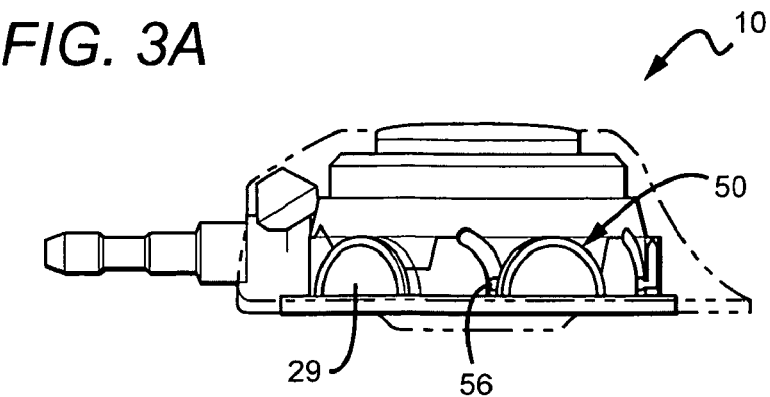
FIG. 3A is a side view of the implantable port of FIG. 1 in an initial position for handling and implanting into a body.

The gear 46 includes gear teeth 45, which interact with the cam 40, on one side and a gear opening 47 on the opposite side. The gear opening 47 is aligned with the second opening 18 in the top 12 and is configured to interact with a tool (not shown) such that inserting the tool into the gear opening 47 permits one to turn the gear 46, which rotates the gear teeth 45, which in turn rotates the cam 40 about the fluid reservoir 22. The rotation of the cam 40, as mentioned above, acts to move the suture needles 50 about the ridges 29. This interaction can be seen from a side view in FIGS. 3A-3C, which again show the top 12 in phantom so that the component parts of the port 10 can be seen. Referring to FIG. 3A, the port 10 is in an initial position for implantation into a body with the suture needles 50 being fully inside the port and the needle posts 56 adjacent the platform 28 on a first side of respective ridges 29. At this stage, the port 10 has a smooth outer profile and can be safely handled by a clinician without fear of coming into contact with a needle point or other sharp edge thereof. Also, at this stage, the suture needles 50 are locked into place by the cam 40.

Figure 3B:
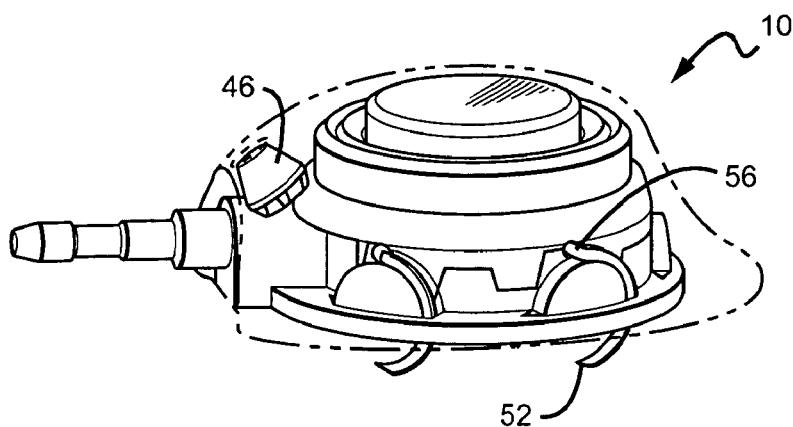
FIG. 3B is a side perspective view of the implantable port of FIG. 3A, following activation of a suturing process.
Figure 3C:
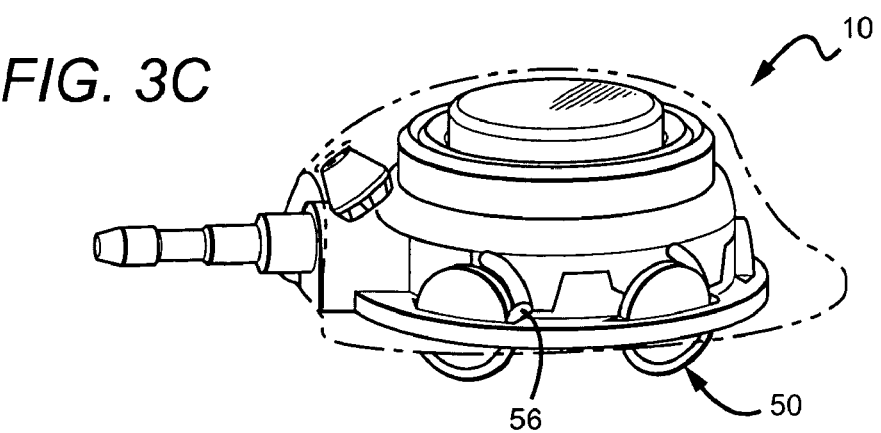
FIG. 3C is a side perspective view of the implantable port of FIG. 3A, following completion of a suturing process.

Using a tool, the gear 46 is rotated in a clockwise direction, which rotates the cam 40 about the fluid reservoir 22, which is situated generally along a central axis of the port, in a counterclockwise direction (of course, the direction of movement could be reversed with respect to the gear 46 and the cam 40). As shown in FIG. 3B, the rotation of the cam 40 causes a distal portion of the suture needles 50 to move through the passageways 27 and out of the bottom of the base 20 as the suture needle posts 56, having at least the enlarged portion thereof positioned in slots in the cam 40, track over a surface of the ridges 29. In the embodiment shown in FIGS. 1-3, the enlarged portion of the needle post 56 is in the form of a ball, which aids in smooth movement over the ridge 29. As the needle tips 52 travel out of the needle passageways 27, their sharp points engage and penetrate tissue of a body in which the port 10 is implanted. It is noted that use of a gear 46 and a cam 40 provide a significant mechanical advantage such that puncturing through tissue is facilitated. Continued movement of the needles 50 through the tissue anchors the port 10 to the body tissue. FIG. 3C illustrates a completed insertion procedure as the suture needle posts 56 have traveled from a first side of respective ridges 29, adjacent platform 28, to a second side, causing the suture needle tips 52 to travel in a similar path through the body tissue such that the port 10 is sutured to the body into which it is implanted. At this stage, the cam 40 acts to lock the suture needles 50 in position to prevent accidental detachment.

Figure 3D:
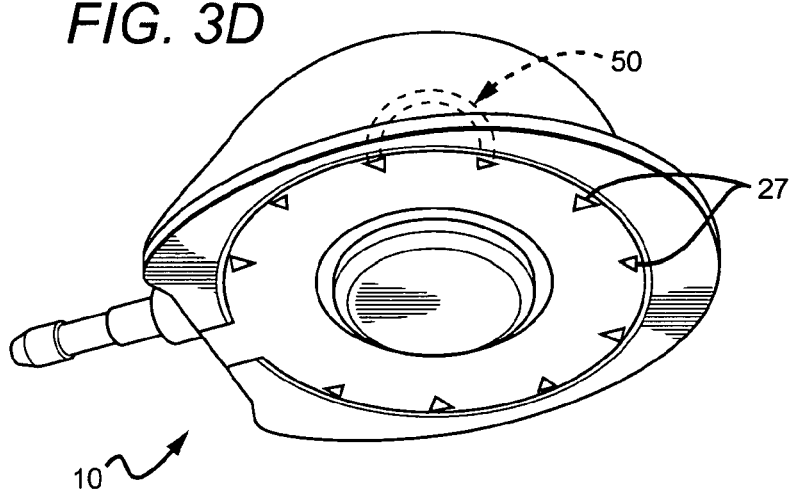
FIG. 3D is a bottom perspective view of the implantable port of FIG. 3A.
Figure 3E:
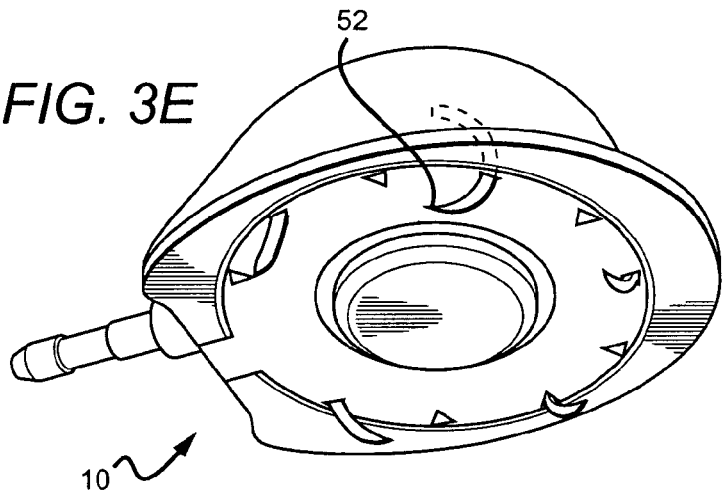
FIG. 3E is a bottom perspective view of the implantable port of FIG. 3A, following activation of a suturing process.
Figure 3F:
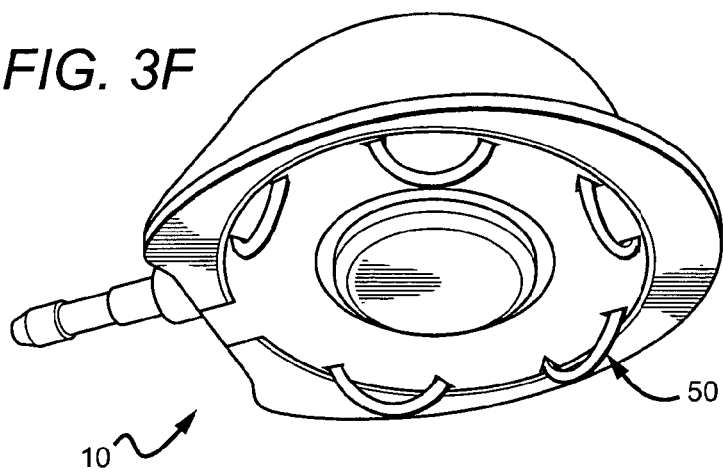
FIG. 3F is a bottom perspective view of the implantable port of FIG. 3A, following completion of a suturing process.

From a bottom view, as shown in FIGS. 3D-3E, as the cam 40 is rotated, suture needle tips 52 emerge from the bottom openings of passageways 27 in base 20 and into adjacent bottom openings such that complete rotation of the cam 40 results in the suture needle tips 52 positioned within passageways 27 (FIG. 3E). In the pre-activation stage (FIG. 3D), it can be seen that the bottom of the port base 20 is smooth in that no sharp points are protruding, meaning that the implantable port can be safely handled. As the port 10 has been activated in FIG. 3D, the needles 50 can be seen to track in a circular path. In the embodiment shown, the needles 50 have a triangular cross-sectional shape for strength and to maintain shape and direction during the activation process. The passageways 27 also have a triangular cross-sectional shape to accommodate the needles 50. In other embodiments, the needles 50, and the corresponding passageways 27, can have different cross-sectional shapes, such as circular, elliptical, square, rectangular, etc. FIG. 3E shows the suture needles 50 after activation is completed, the distal tips 52 entering into openings in the bottom of the port base 20 such no sharp tips 52 remain in the tissue, which can potentially lead to infection and/or patient discomfort.

FIG. 4 shows a variation of the port shown in FIGS. 1-3. Implantable port 60 includes a cam 62 that is a single component as opposed to the dual component cam 40. Cam 62 includes slots 64 that are arranged vertically adjacent one side of respective ridges 29, the slots 64 configured to receive at least a portion of the suture needle posts 56. As the cam 62 rotates about the fluid reservoir 22, the slots 64 track from one side of respective ridges 29 to the opposite side and the posts, also tracking along the ridges 29, move from a lower portion of the slots 64 to an upper portion thereof and back down as the slots 64 rotate to the opposite side of the ridges 29. As discussed above, when the posts 56 move along the ridges 29, the suture needle tips 52 move through the passageways 27, through the body tissue, and back into the passageways through adjacent openings in the bottom of the port base 20. The use of a single component cam 62 is believed to facilitate retraction of the suture needles as the cam is moved in the opposite (i.e., clockwise) direction.

Figure 6:
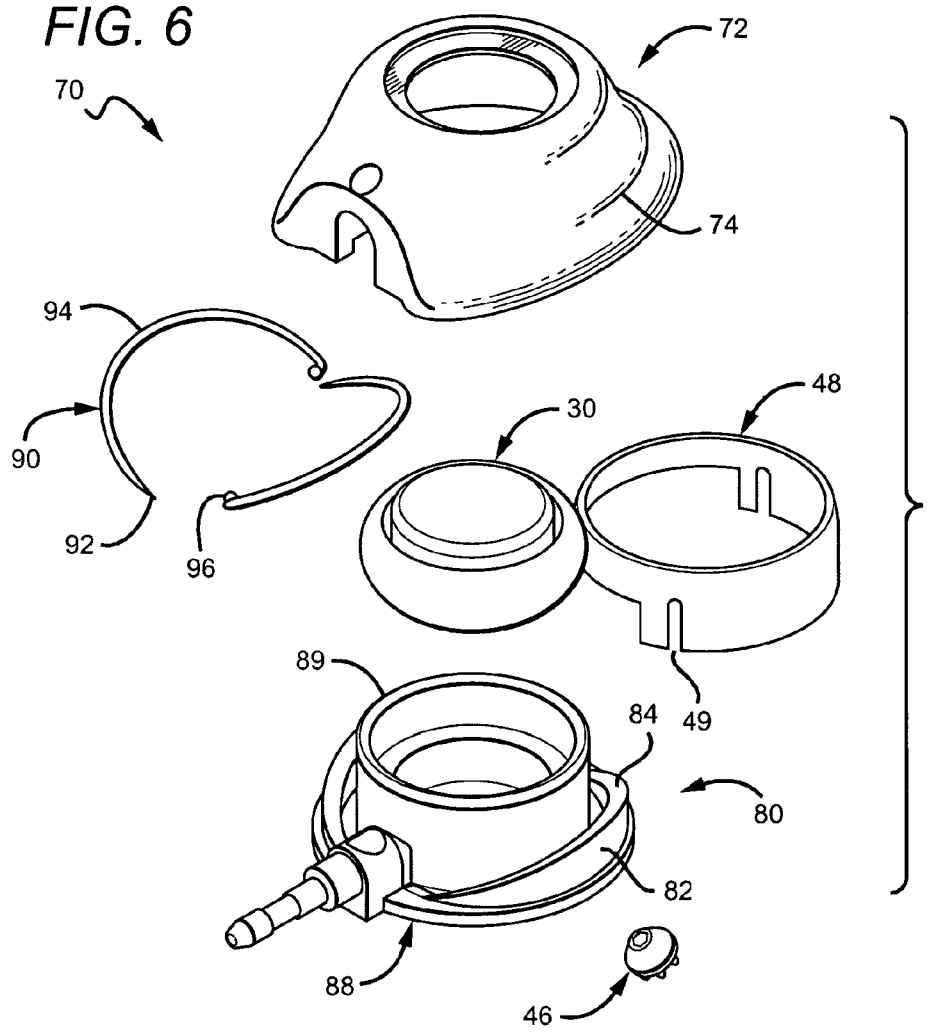
FIG. 6 is an exploded view of the implantable port of FIG. 5.

FIGS. 5-7 illustrates another embodiment of an implantable port. FIG. 5 shows implantable port 70 assembled with the top 12 of the port 70 in phantom to show the components thereof, while FIG. 6 is an exploded view of the implantable port 70. Implantable port 70, similarly to implantable port 10 and 60, includes a top 12, a septum 30 and a gear 46. However, implantable port 70 includes a different base and needle configuration. As seen best in FIG. 6, the base 80 includes a pair of opposing ramps 82 configured for the two needles 90, which include needle tips 92, needle bodies 94 and needle posts 96. The posts 96 include enlarged distal sections that in this embodiment are shown in the form of balls, which aid in smooth movement over the ramps 82. Each of the needles 90 sit on a top surface 84 of the ramp 84, the surface 84 being angled toward the fluid reservoir 22 to facilitate movement of the needle 90 thereover. The cam 48 includes two slots for receiving the enlarged portion of the posts 96. In an initial position for implantation into a body, shown in FIG. 5, the suture needles 90 are within the port 70 and the needle posts 96 are adjacent the platform 88 of the port 70 within the slots 49 of the cam 48. At this stage, the port 70 has a smooth outer profile and can be safely handled by a clinician without fear of coming into contact with a needle point or other sharp edge thereof. Also, at this stage, the suture needles 90 are locked into place by the cam 48.

Using a tool, the gear 46 is rotated in a clockwise direction, which rotates the cam 48 about the fluid reservoir 22 in a counterclockwise direction (of course, the direction of movement could be reversed with respect to the gear 46 and the cam 48). Rotation of the cam 48 causes a distal portion of the suture needles 90, including the needle tips 92 to move through passageways and out of the bottom of the base 80 as the suture needle posts 96 track over the surface 84 of the ramps 82. As the needle tips 92 travel out of the needle passageways, they engage tissue of a body in which the port 70 is implanted. Continued movement of the needles 90 through the tissue as the cam 48 is rotated anchors the port 70 to the body tissue. At this stage, the cam 48 acts to lock the suture needles 90 in position to prevent accidental detachment. FIG. 7B is a bottom view of the port 70 following complete rotation of the cam 48 such that the suture needle posts 96 have traveled from a first side of respective ramps 82 adjacent platform 88, to a second side, causing the suture needle tips 92 to travel in a similar path through the body tissue. As shown in FIG. 7B, the suture needle tips 92 emerge upon initiation of the suturing process from first openings 85 and, upon completion of the suturing process, enter into second openings 86. In this embodiment, the second openings 86 have a cross-sectional area larger than the first openings 85 and can be filled with silicone or a like material, providing a larger target for the suture needles in the event that they are bent or otherwise prevented from reaching the openings 86. In addition, the openings 86 may be tapered to facilitate entry of the suture needle tips 92. FIG. 7A is a front view of the port 70 following completion of the suturing process.

Applicant believes that notable benefits to the embodiment shown in FIGS. 5-7 include, for example, a minimum of component parts, very good tissue penetration without penetrating deep into the patient's tissue due to suture needle and track configuration, and flexible suture needle design, which aids in patient comfort. The suture needles 90 are much longer and can have a larger diameter than the suture needles 50 such that at least some of the aforementioned benefits are achieved. The suture needles 90 in one embodiment are flexible and/or rounded to decrease pain or patient discomfort. Further, the port 70 can be easily removed from the body in which it is implanted by simply turning the gear 46 in the opposite direction (i.e., counterclockwise), which rotates the cam 48 in a clockwise direction, thereby withdrawing the needles from second openings 86 and back through openings 85 until fully within the port 70. Also, because the gear can be positioned on the port for easy access following implantation of the port within a subcutaneous pocket, a smaller pocket may be utilized as the port can be attached by simply inserting a tool into the gear and rotating the gear as described.

Moreover, as best seen in FIG. 7A, the top 72 includes gripping bumps 74 on an outer surface, which in this embodiment are subtle indentations in the outer surface of the port top 72 to facilitate the handling of the port 70 by the clinician. Other types of gripping surfaces are also possible to assist in the handling of the port 70 and are within the scope of this invention. It should be appreciated that gripping bumps and/or gripping surfaces can be incorporated to any of the implantable ports of this invention. Applicant recognizes that the features of the port top 12 and 72, including an opening and conical seat for the gear 46, indentations to receive the ridges 29 or ramps 82, gripping bumps 74, etc., are moldable with a single-direction mold. Also, as shown and described in commonly assigned U.S. patent application Ser. No. 11/189, 577, which is incorporated by reference into this application as if fully set forth herein, the port 70 can include an energy director positioned on a top surface 89 of the port base 80 and a corresponding flat on the underside of the port top 72 such that far field welding may be utilized to weld a joint between the port top 72 and the port base 80.

Figure 8A:
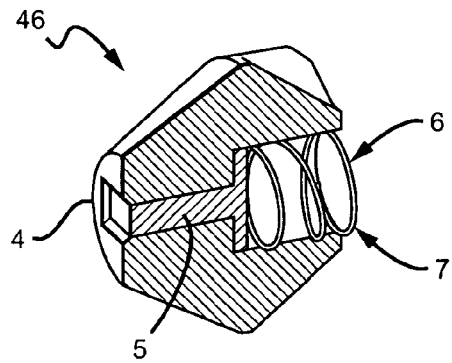
FIG. 8A is a cross-sectional view of an embodiment of a gear of an implantable port in a position prior to activation.
Figure 8B:
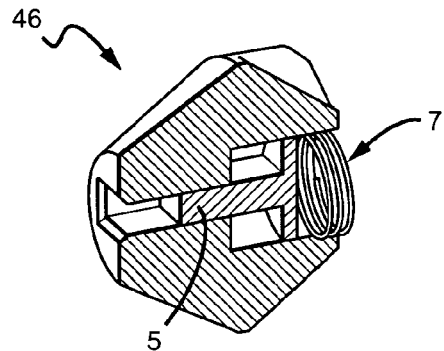
FIG. 8B is a cross-sectional view of the gear of FIG. 8A in an activation position.

FIGS. 8A and 8B illustrate one type of mechanism for incorporation into gear 46. Gear 46 is shown in a partial cross-sectional view without the gear teeth 45. The gear 46 has a frusto-conical shaped top and a throughgoing lumen that extends from an opening 4 in the top to an opening 6 in the base. The lumen has a cross-sectional area in the base region larger than in the top region. The opening 4 is rectangular, but can be of any shape, configured to receive a tool therethrough (e.g., hexagonal, cross-shaped, circular, etc.). Positioned within the lumen of the gear 46 is a tab member 5, which in the embodiment shown is T-shaped, but depending on the cross-sectional shape of the lumen, could be shaped differently. The T-shaped member has a narrow portion thereof in the lumen of the top region and a wide portion thereof in the lumen of the bottom region of the gear 46, the wide portion of the tab member 5 having a cross-sectional area larger than the cross-sectional area of the lumen of the top region to prevent entering therein. In this embodiment, the top portion of the tab member is configured to fit snugly within the lumen of the top region. A spring or compression member 7 is positioned within the lumen bottom region against the wide portion of the tab member 5. To activate, a tool is inserted into the opening 4, pressing the tab member 5 inward a sufficient distance for rotation of the gear 46 by the tool (i.e., the tool is inserted a sufficient distance to provide a mechanical advantage to a twisting motion thereof), which acts to rotate the cam and initiate the suturing process. When the tool is removed from the lumen of the gear 46, the spring member 7 presses the tab member 5 back toward the opening 4 such that the opening 4 is closed to fluid or bodily tissue. Due to the simplicity of this design, the gear 46 can be activated to suture a port to a body without complicated and/or specialty instruments.

In another embodiment of an implantable port, a single needle could be utilized to anchor the port to a body into which it is implanted. For example, a suture needle having a preformed shape that defines the path of the suture needle is wound around a section of the port base (e.g., the fluid reservoir) in a manner similar to a tape measure. Movement of the suture needle out of the port base and into the patient's tissue involves rotation of a movable member, which in one embodiment is the port base itself or a section thereof, and which in another embodiment is a geared ring that is attached to the end of the suture needle and is configured to rotate around the port base in a manner similar to that of the cam, as described herein (e.g., is connected to a gear or other mechanism that when activated causes movement of the movable member).

In one embodiment, the suture needle is fixed, having an initial relaxed state within the implantable port. A tensioning member is positioned adjacent a section of the port base such that the suture needle is positioned between the tensioning member and the port base section. Movement of the suture needle out of the bottom or side of the port base and into the patient's tissue involves rotation of the tensioning member around the section of the port base and against the suture needle along a length thereof. As the tensioning member moves along the length of the needle in a distal direction with respect thereto (being initially positioned at the proximal end thereof), tension is applied to the needle, which is flexible, forcing movement in the distal direction of the portion of the needle distal the tensioning member. Retraction of the needle involves movement of the tensioning member along the length of the needle in a proximal direction, which removes the tension and permits the suture needle to resume its relaxed state within the port. Each of the embodiments mentioned above may be activated through the use of a gear type mechanism as disclosed herein.

In another embodiment, the suture needle is fixed, having an initial relaxed state within the implantable port, and is connected to a pull-tab that extends out of the port. When the port has been implanted and activation is desired to attach the port to the patient, the clinician applies force to the pull-tab (e.g., pulls the pull-tab in a direction away from the port), causing the suture needle to become tensioned, thereby forcing the distal end of the suture needle out of the port base and into the patient's tissue. A latching mechanism is then activated upon full extension of the tab out of the port and the pull-tab detaches so that it can be discarded. When deactivation of the implantable port is desired to remove the implantable port from the patient, a tool is utilized to release the latching mechanism such that the tension is removed from the suture needle, whereby the suture needle resumes its relaxed state and retracts back into the implantable port. The implantable port can be fashioned such that either a standard tool or a specialized tool can be utilized to release the latching mechanism. Although the embodiments are described with respect to single suture needles, two or more needles could also be incorporated into these embodiments. Also, the ports can be configured to have the suture needle(s) project from a side of the port, rather than from the bottom of the port base. For example, the suture needle(s) could extend parallel to the bottom of the port base or at an angle with respect thereto.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A method for attaching an access port to a patient, comprising:
   providing an access port including:
      a port base having a fluid reservoir defined by a cylindrical wall, a first ramp with a first arc positioned adjacent an outer surface of the fluid reservoir wall on a first side, and a second ramp with a second arc positioned adjacent the outer surface of the fluid reservoir wall on a second side opposite of the first side;
      a septum positioned over the fluid reservoir;
      a port top positioned over the septum and the port base;
      a first suture needle having a curved shape matching the first arc and positioned on a surface of the first ramp;
      a second needle having a curved shape matching the second arc and positioned on a surface of the second ramp; and
      a movable member comprising a cam positioned about the fluid reservoir wall and having separate first and second engagement features to respectively engage portions of the first and second suture needles, the first and second engagement features including respective first and second slots, wherein respective portions of the first and second suture needles are slidingly positioned in the first and second slots, the cam connected to a gear including an opening and a tab member biased in the opening by a compression member;
   inserting a tool into the opening to move the tab member out of the opening and transition the gear from a locked position to an open position; and
   rotating the movable member around the fluid reservoir wall to move the first and second suture needles, respectively, over the surfaces of the first and second ramps.

2. The method according to claim 1, wherein the port top comprises one or more gripping surfaces, further comprising the steps of forming a subcutaneous pocket in the patient's body, gripping the access port on said gripping surfaces, and inserting the access port into the subcutaneous pocket.

3. The method according to claim 1, wherein the port base includes a first passage adjacent an end of the first ramp and a second passage adjacent an end of the second ramp, the rotating step further comprising passing portions of the first and second suture needles, respectively, through the first and second passages.

4. The method according to claim 3, wherein the port base includes first and second openings positioned to respectively receive a distal tip of the first and second suture needles, the rotating step further comprising moving the distal tips of the first and second suture needles, respectively, through the first and second passages.

5. The method according to claim 4, wherein the first opening is positioned adjacent the second passage and the second opening is positioned adjacent the first passage.

6. The method according to claim 4, wherein the first and second openings have a cross-sectional area respectively larger than a cross-sectional area of the first and second passages.

7. The method according to claim 4, wherein the first and second openings respectively have a cross-sectional area larger than a cross-sectional area of the first and second passages.

8. The method according to claim 4, wherein each of the first and second openings is filled with a silicone material.

9. The method according to claim 4, wherein each of the first and second openings is tapered.

10. The method according to claim 1, wherein at least one of the first and second suture needles is flexible.

11. The method according to claim 1, wherein the surfaces of the first and second ramps are angled toward the fluid reservoir.

* * * * *